United States Patent
Chen et al.

(10) Patent No.: US 9,431,258 B1
(45) Date of Patent: Aug. 30, 2016

(54) METHOD FOR PHOTODEPOSITING A PARTICLE ON A GRAPHENE-SEMICONDUCTOR HYBRID PANEL AND A SEMICONDUCTOR STRUCTURE

(71) Applicant: NATIONAL SUN YAT-SEN UNIVERSITY, Kaohsiung (TW)

(72) Inventors: Chun-Hu Chen, Kaohsiung (TW); Cheng-Chi Kuo, Kaohsiung (TW)

(73) Assignee: NATIONAL SUN YAT-SEN UNIVERSITY, Kaohsiung (TW)

(*) Notice: Subject to any disclaimer, the term of this patent is extended or adjusted under 35 U.S.C. 154(b) by 0 days.

(21) Appl. No.: 14/666,948

(22) Filed: Mar. 24, 2015

(30) Foreign Application Priority Data

Feb. 9, 2015 (TW) .............................. 104104224 A

(51) Int. Cl.
*H01L 51/00* (2006.01)
*H01L 43/02* (2006.01)
*H01L 21/288* (2006.01)
*G01N 33/543* (2006.01)

(52) U.S. Cl.
CPC ....... *H01L 21/288* (2013.01); *G01N 33/54373* (2013.01)

(58) Field of Classification Search
CPC .............. H01L 2924/0002; H01L 23/53276; H01L 2924/00; H01L 51/0048; H01L 51/0002; H01L 51/0045
See application file for complete search history.

(56) References Cited

U.S. PATENT DOCUMENTS

| | | | | |
|---|---|---|---|---|
| 2012/0021249 A1* | 1/2012 | Shin | ...................... | B82Y 30/00 428/688 |
| 2013/0153860 A1* | 6/2013 | Kim | ................... | H01L 51/0002 257/14 |
| 2013/0192461 A1* | 8/2013 | Miller | ................ | B01D 67/0039 95/47 |
| 2014/0233297 A1* | 8/2014 | Ozyilmaz | ............. | B82Y 10/00 365/145 |

OTHER PUBLICATIONS

Cheng-Chi Kuo et al,"Graphene thickness-controlled photocatalysis and surface enhanced Raman scattering", Nanoscale, Aug. 26, 2014, 6, pp. 12805-12813.*

* cited by examiner

*Primary Examiner* — Thomas L Dickey
*Assistant Examiner* — Damon Hillman
(74) *Attorney, Agent, or Firm* — Muncy, Geissler, Olds & Lowe, P.C.

(57) ABSTRACT

A method for photodepositing a particle on a graphene-semiconductor hybrid panel is disclosed. The method for photodepositing the particle on the graphene-semiconductor includes providing a graphene-semiconductor hybrid panel, dipping the graphene-semiconductor hybrid panel in a fluid containing a precursor, and irradiating the graphene-semiconductor hybrid panel using a light source until the precursor has been reduced or oxidized to form a particle photodeposited on a surface of a graphene sheet. The graphene-semiconductor hybrid panel includes a semiconductor substrate and the graphene sheet adhered to the semiconductor substrate. The light source has an energy equal to or higher than a band gap of the semiconductor substrate. As such, the particle can be directly deposited on the surface of the graphene sheet without the need of modifying the graphene.

8 Claims, 5 Drawing Sheets

METHOD FOR PHOTODEPOSITING A PARTICLE ON A GRAPHENE-SEMICONDUCTOR HYBRID PANEL AND A SEMICONDUCTOR STRUCTURE

BACKGROUND OF THE INVENTION

1. Field of the Invention

The present invention generally relates to a method for depositing a particle on a graphene-semiconductor hybrid panel and a semiconductor structure and, more particularly, to a method for photodepositing a particle on a graphene-semiconductor hybrid panel and a semiconductor structure.

2. Description of the Related Art

Graphene is a light-weighted material with high hardness, high carrier mobility, and high heat conductivity. Hence, the applications of graphene are highly expected after it has been successfully produced. Depositing particles on the surface of graphene may result in further improvement of the utility of graphene. For example, the graphene having gold particles deposited on its surface is capable of detecting biomedical targets, such as DNA and viruses.

However, according to a conventional method for depositing a gold particle on a surface of a graphene, the gold particle can only be deposited on a modified graphene, such as a graphene having a functional group on its surface. The modification process is inconvenient, and the gold particle still has to be deposited through complicated chemical reactions. Since the gold particle is bonded to the functional group instead of directly bonded to the surface of the graphene, the adhesion of the gold particle and the graphene is weak, and may easily be broken by an external force. Furthermore, because of the modification site is located randomly on the surface of the graphene, the deposited gold particle may not be exactly on the charge transfer site, which results in a low charge transfer efficiency. Moreover, the charge transfer efficiency may further be reduced by the functional group located between the deposited gold particle and the surface of the graphene. As such, the utility of the gold-deposited graphene is limited.

SUMMARY OF THE INVENTION

It is therefore the objective of this invention to provide a method for photodepositing a particle on a graphene-semiconductor hybrid panel for directly depositing a particle on a surface of a graphene without the need of modifying the graphene.

It is another objective of this invention to provide a method for photodepositing a particle on a graphene-semiconductor hybrid panel for precisely depositing a particle on a charge transfer site of a graphene.

It is still another objective of this invention to provide a semiconductor structure having a particle directly deposited on a surface of a graphene.

The present invention provides a method for photodepositing a particle on a graphene-semiconductor hybrid panel, including providing a graphene-semiconductor hybrid panel, dipping the graphene-semiconductor hybrid panel in a fluid containing a precursor, and irradiating the graphene-semiconductor hybrid panel using a light source till the precursor has been reduced or oxidized to form a particle deposited on a surface of a graphene sheet. The graphene-semiconductor hybrid panel includes a semiconductor substrate and the graphene sheet adhered to a surface of the semiconductor substrate. The light source has an energy equal to or higher than a band gap of the semiconductor substrate.

In a form shown, the graphene sheet is made by chemical vapor deposition and wet transfer.

In the form shown, the semiconductor substrate is made of titanium dioxide or zinc oxide.

In the form shown, the graphene sheet is formed of a graphene layer or a plurality of graphene layers.

In the form shown, the graphene sheet is formed of three graphene layers.

In the form shown, the particle is made of metal, alloy, or metal oxide.

In the form shown, the particle is made of gold, silver, or manganese dioxide.

In the form shown, the graphene sheet is made by chemical vapor deposition and wet transfer, the semiconductor substrate is made of titanium dioxide, the graphene sheet is formed of three graphene layers, and the particle is made of gold.

The present invention further provides a semiconductor structure including a semiconductor substrate, a graphene sheet, and a particle. The graphene sheet has a first surface and a second surface opposite to the first surface. The first surface of the graphene sheet is adhered to the semiconductor substrate. The particle is deposited on the second surface of the graphene sheet. The semiconductor substrate is made by the method for photodepositing the particle on the graphene-semiconductor hybrid panel of the present invention.

In the method for photodepositing the particle on the graphene-semiconductor hybrid panel, the semiconductor substrate is irradiated by the light source for generating the photoinduced electron and hole, and then the electron and hole are transferred to the graphene sheet. The precursor is reduced or oxidized by the electron or the hole to form the particle directly deposited on the surface of the graphene sheet. Thus, the function of directly depositing the particle on the surface of the graphene is achieved.

By using the method for photodepositing the particle on the graphene-semiconductor hybrid panel in the present invention, the particle is deposited on the surface of the graphene sheet by irradiation using the light source. Thus, the process of depositing the particle on the graphene sheet is simplified without the need of modifying the graphene.

Furthermore, according to the method for photodepositing the particle on the graphene-semiconductor hybrid panel in the present invention, the precursor is reduced or oxidized by the electron or hole generated in the semiconductor substrate and transferred by the graphene sheet. As such, the particle is deposited directly on the charge transfer site of the graphene sheet, thus providing an excellent charge transfer efficiency of the particle.

In addition, according to the method for photodepositing the particle on the graphene-semiconductor hybrid panel in the present invention, since the particle is deposited on the graphene-semiconductor hybrid panel by irradiation using the light source, the light source may be controlled to irradiate only a specific area to deposit the particle in the specific area. The method for photodepositing the particle on the graphene-semiconductor hybrid panel of the present invention is also capable of depositing the particle on a large-sized graphene sheet.

With accordance to the semiconductor structure in the present invention, since the particle is directly deposited on the surface of the graphene sheet, the charges may directly be transferred between the graphene sheet and the particle without flowing through the functional group, which is necessary in the conventional method. Thus, the electrochemical activity of the particle is improved.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

Figure 1:
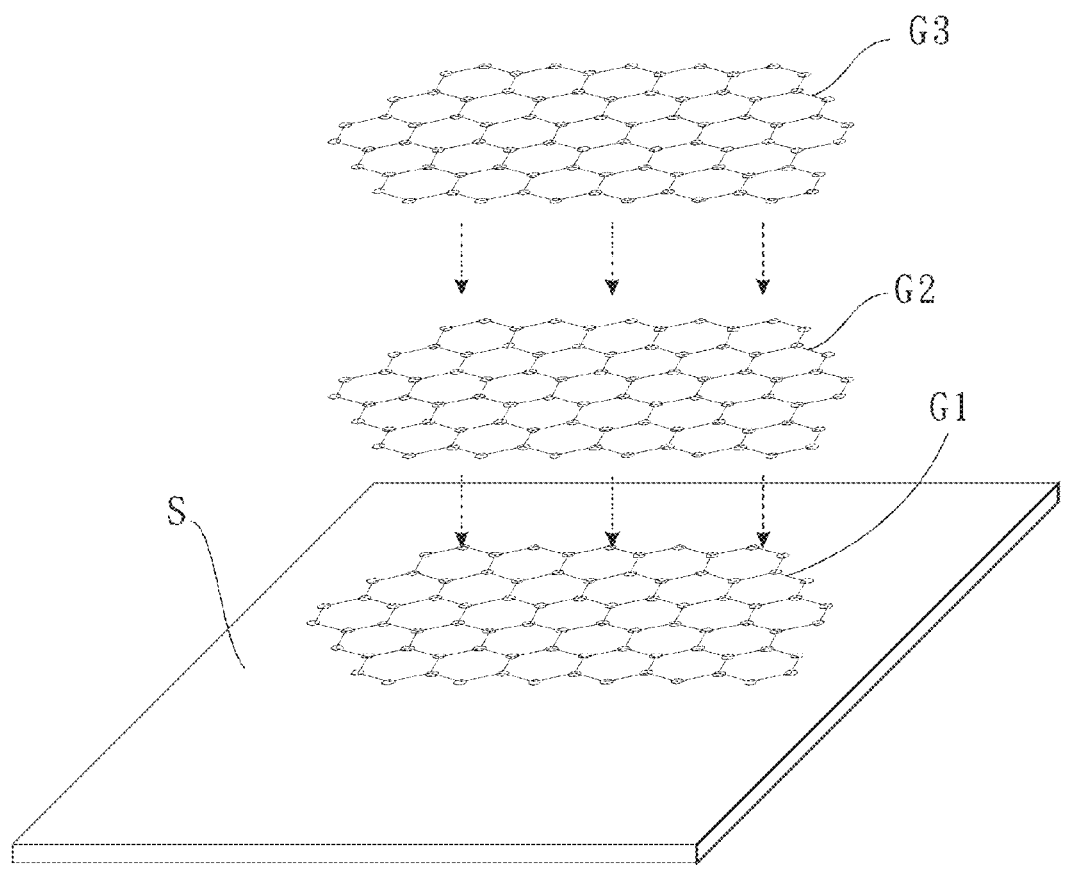
FIG. 1 illustrates a fabricating procedure of a graphene-semiconductor hybrid panel according to the present invention.

In the various figures of the drawings, the same numerals designate the same or similar parts. Furthermore, when the terms "first", "second", "third", "fourth", "inner", "outer", "top", "bottom", "front", "rear" and similar terms are used hereinafter, it should be understood that these terms have reference only to the structure shown in the drawings as it would appear to a person viewing the drawings, and are utilized only to facilitate describing the invention.

DETAILED DESCRIPTION OF THE INVENTION

A method for photodepositing a particle on a graphene-semiconductor hybrid panel according to the present invention includes providing a graphene-semiconductor hybrid panel having a semiconductor substrate and a graphene sheet, dipping the graphene-semiconductor hybrid panel in a fluid, and irradiating the graphene-semiconductor hybrid panel for photodepositing a particle on a surface of the graphene sheet. Thus, the particle can be deposited on the surface of the graphene sheet without the need of modifying the graphene.

In more detail, the graphene sheet is adhered to a surface of the semiconductor substrate, thus forming the graphene-semiconductor hybrid panel. The semiconductor substrate may be, but not limited to, silicon dioxide ($SiO_2$), silicon nitride ($Si_3N_4$), aluminum oxide ($Al_2O_3$), titanium dioxide ($TiO_2$), tantalum (III) oxide ($Ta_2O_3$), zinc oxide (ZnO), hafnium (IV) oxide ($HfO_2$), zirconium dioxide ($ZrO_2$), lanthanum oxide ($La_2O_3$), yttrium (III) oxide ($Y_2O_3$), cadmium oxide ($Cd_2O_3$), erbium oxide ($Er_2O_3$), neodymium (III) oxide ($Nd_2O_3$), praseodymium (IV) oxide ($PrO_2$), cerium (IV) oxide ($CeO_2$), gallium nitride (GaN), gallium arsenide (GaAs), zinc sulfide (ZnS), indium nitride (InN). The graphene sheet may be produced by chemical vapor deposition, mechanical exfoliation, chemical exfoliation, or epitaxial growth, and may be formed of a single graphene layer as well as a plurality of graphene layers stacked together. It is noted that the graphene sheet in the present invention can be made by any process, and the thickness, homogeneity, and number of layers of the graphene sheet are not limited. In this embodiment, a graphene layer is initially chemical vapor deposited, and than being wet transferred to the semiconductor substrate. The graphene layer produced by chemical vapor deposition can advantageously have a uniform thickness and homogeneity. In addition, the graphene sheet formed of a plurality graphene layers can be easily produced by repeating the wet transfer step. The thickness of the single graphene layer may be of 0.6-1.5 nm, and preferably of 0.8-0.9 nm.

Specifically, the graphene layer in this embodiment may be produced on a copper foil by chemical vapor deposition under a low pressure condition. The copper foil is placed in a quartz tube at $10^{-3}$ Torr, then, the chemical vapor deposition system is heated up to 1000° C. with a flow of hydrogen gas at 10 sccm for 20 minutes for cleaning and annealing the surface of the copper foil. Next, the atmosphere inside the chemical vapor deposition system is changed to a mixture of $CH_4$ at 10 sccm and $H_2$ at 35 sccm for 40 minutes. Finally, the chemical vapor deposition system is cooled to room temperature under argon flow at 60 sccm. The graphene layer produced on the copper foil is coated by a thin layer of poly(methyl methacrylate) (PMMA) before the copper foil is etched away with an ammonium persulfate aqueous solution. The graphene layer coated by the thin layer of PMMA is then transferred to the surface of the semiconductor substrate, followed by removing the thin layer of PMMA using an organic solvent, such as toluene. Thus, the graphene layer is produced and adhered to the surface of the semiconductor substrate, and the graphene-semiconductor hybrid panel is obtained. Please refer to FIG. 1, after a first graphene layer "G1" has been adhered to the semiconductor substrate "S," another graphene layer "G2" coated by the thin layer of PMMA can be wet transferred to a surface of the graphene layer "G1," and the thin layer of PMMA may be removed to form a second graphene layer "G2" on the graphene-semiconductor hybrid panel. By repeating the above steps, the graphene-semiconductor hybrid panel may be produced with the graphene sheet "G" formed of a plurality of graphene layers, such as the graphene layer marked "G1," "G2" and "G3" shown in FIG. 1.

The fluid includes a precursor of the particle. The precursor contains a cation, an anion, or a molecule, which can be reduced or oxidized by an electron or a hole to form the particle. In addition, the precursor may contain two or more kinds of ions and/or molecules for the purpose of depositing different particles at the same time. Specifically, the particle may be made of metal or alloy, such as gold, silver, copper, iron, cadmium, zinc, cobalt, nickel, chromium, aluminum, magnesium, gold-silver alloy, silver-copper alloy. Moreover, the particle may be made of metal oxide, such as manganese dioxide, cobalt oxide, iron oxide, silicon dioxide, copper oxide, zinc oxide, magnesium oxide, and zirconium dioxide. However, this is not to be taken as a limited sense. The precursor is selected corresponding to the elemental composition of the particle. For example, the precursor may be a metal ion, which can be reduced to form the particle of metal, as it would be understood by the persons ordinarily skilled in the art. The fluid may be a solvent or a gel for dissolving the precursor without damaging the semiconductor substrate.

Figure 2:
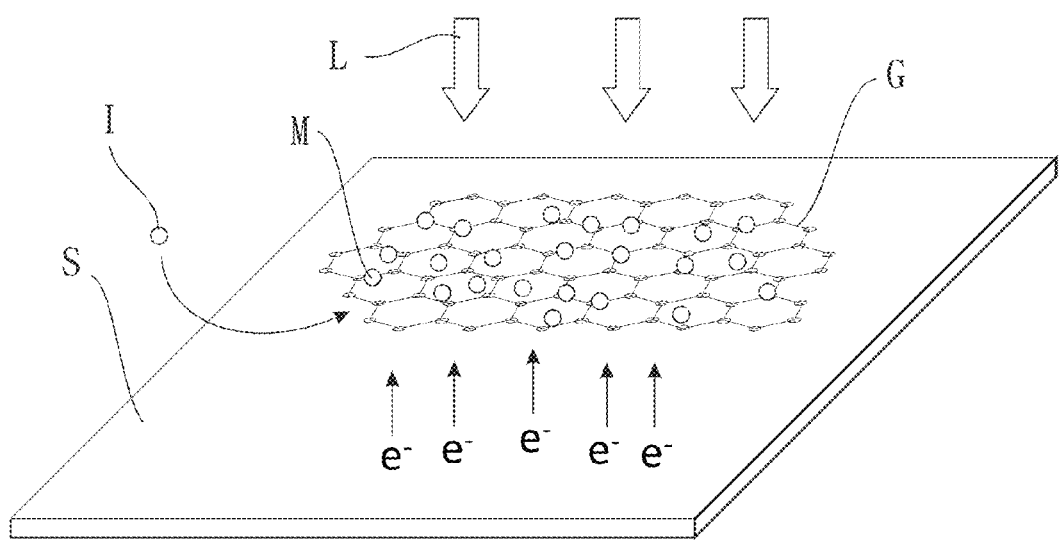
FIG. 2 illustrates a mechanism of a method for photodepositing a particle on a graphene-semiconductor hybrid panel according to the present invention.
Figure 3:
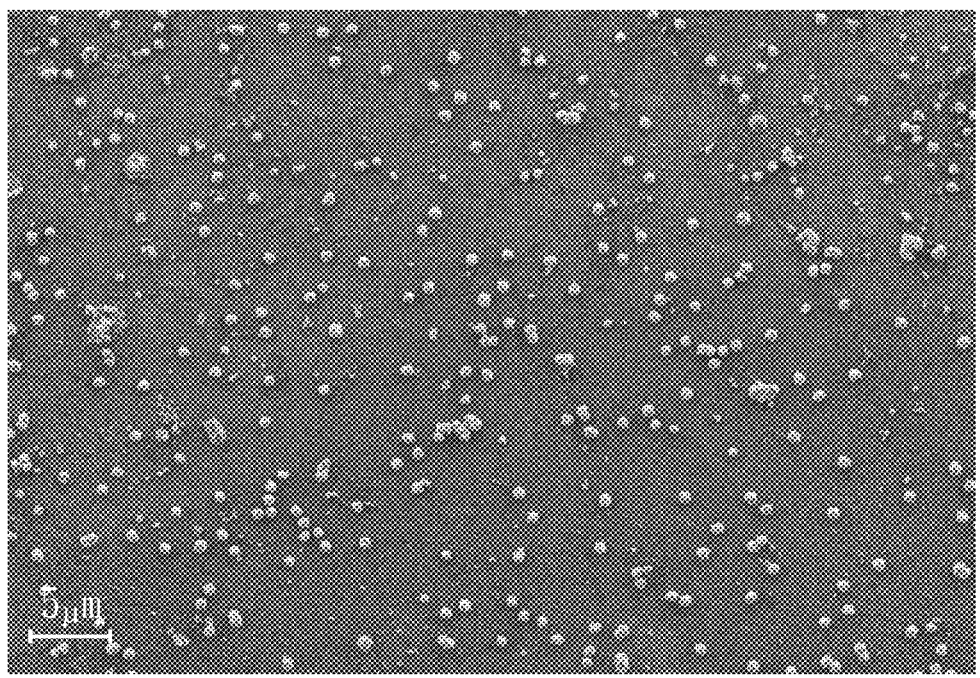
FIG. 3 is a SEM image of the experimental result of Group A1.

The light source refers to any radiation form with energy for exciting the electrons or holes in the semiconductor substrate. Specifically, the light source may have an energy equal to or higher than the band gap of the semiconductor. For example, the light source may be UV light with a wavelength of 365 nm for the semiconductor made of titanium oxide or zinc oxide. Furthermore, a user can control the light source to irradiate only a specific area on the graphene-semiconductor hybrid panel for photodepositing the particle inside the specific area. Please refer to FIG. 2, which shows the mechanism of the method for photodepositing the particle on the graphene-semiconductor hybrid panel. The graphene-semiconductor hybrid panel is dipped in the fluid and surrounded by the precursor "I". Next, the graphene-semiconductor hybrid panel is irradiated and excited by the light source "L", thus generating the photoinduced electrons and holes in the semiconductor substrate "S." The electrons or holes then transfer to the graphene sheet "G" and reduce or oxidize the precursor "I" to form the particle "M" deposited on the surface of the graphene "G" Since the precursor can only be reduced or oxidized at a site capable of charge transferring, the particle is therefore precisely deposited on a charge transfer site of the graphene, which results in an excellent charge transfer efficiency. Moreover, by controlling the size of the graphene sheet and the irradiating area of the light source, the method for photodepositing the particle on the graphene-semiconductor hybrid panel may be easily applied to a large-sized graphene-semiconductor hybrid panel.

As such, the method for photodepositing the particle on the graphene-semiconductor hybrid panel of the present invention can directly deposit the particle on the surface of the graphene sheet without the need of modifying the graphene sheet.

The present invention further provides a semiconductor structure including a semiconductor substrate, a graphene sheet and a particle. The graphene sheet has a first surface and a second surface opposite to the first surface. The first surface of the graphene sheet is adhered to the semiconductor substrate, and the particle is deposited on the second surface of the graphene sheet. The semiconductor structure is produced by the method for photodepositing the particle on the graphene-semiconductor hybrid panel as described in the above. As such, the particle is precisely deposited on the charge transfer site, thus providing excellent charge transfer efficiency and photochemical activity of the semiconductor structure. Therefore, the semiconductor may be applied in the electrochemical field. For example, the semiconductor structure in the present invention is capable of biomedical detection, multi-component mixed catalysis, solar cell, flexible flat panel display, touch panel, semiconductor element coating layer, thermal conductive pad, high-performance display, transparent conductive thin film, ambient light sensor, fuel cell, lithium cell, high-performance transistor, water or pollution filtration, wireless communication, and high-speed transistor.

The particle is selected corresponding to the application of the semiconductor. For example, the particle may be made of an organic material for photocatalysis or solar cell. On the other hand, the semiconductor structure with the particle made of metal or metal oxide, such as gold or silver, may have an excellent surface-enhanced Raman scattering (SERS) efficiency for an SERS substrate of detecting biomedical targets such as DNA and virus.

For validating the function of the method for directly depositing the particle on the surface of the graphene-semiconductor hybrid panel, several experiments are carried out as follows.

In Group A1, A2, and A3 of the first experiment, the graphene-semiconductor hybrid panels with single-layer, 3-layer and 7-layer graphene sheet are produced using chemical vapor deposition and wet transfer method as described in the above with the semiconductor substrate being titanium oxide. Another graphene-semiconductor hybrid panel having 3-layer graphene sheet is produced and treated with oxygen plasma for 5 seconds with a power of 10W under a low-pressure oxygen atmosphere ($2.1 \times 10^{-1}$ Torr) as the graphene-semiconductor hybrid panel of Group A4.

An ethanol solution of 0.001 M chloroauric acid is used as the fluid, which contains a gold ion as the precursor. The graphene-semiconductor hybrid panels of Group A1-A4 are individually placed in quartz tubes, and the fluid is respectively added in every quartz tube. Next, these graphene-semiconductor hybrid panels are irradiated by the light source to photodeposit the gold particle on the surface of the graphene sheet. The light source used in this experiment is a UV light of 365 nm and 16W.

Figure 4:
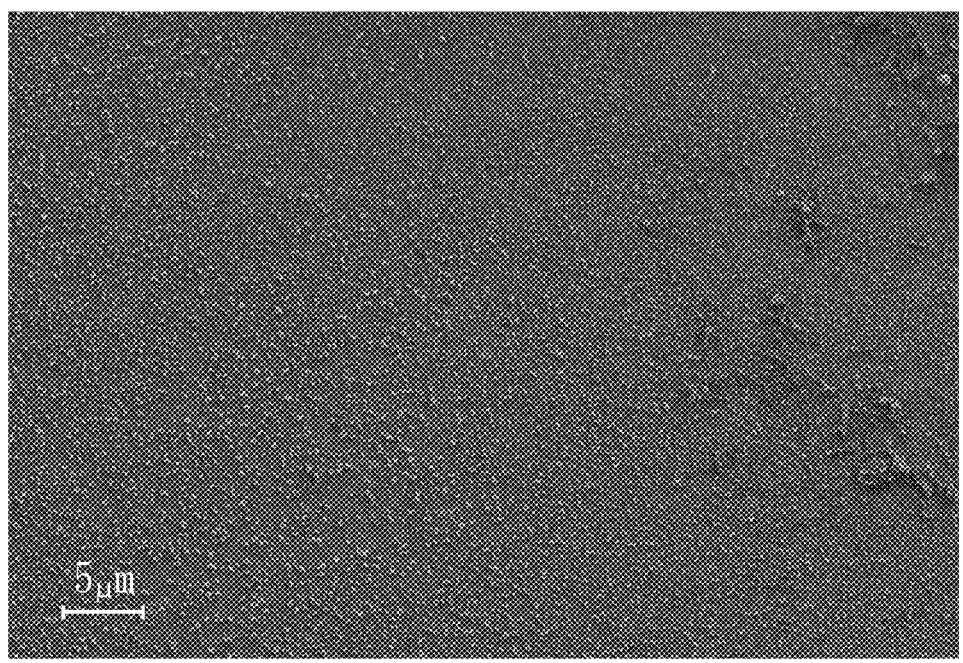
FIG. 4 is a SEM image of the experimental result of Group A2.
Figure 5:
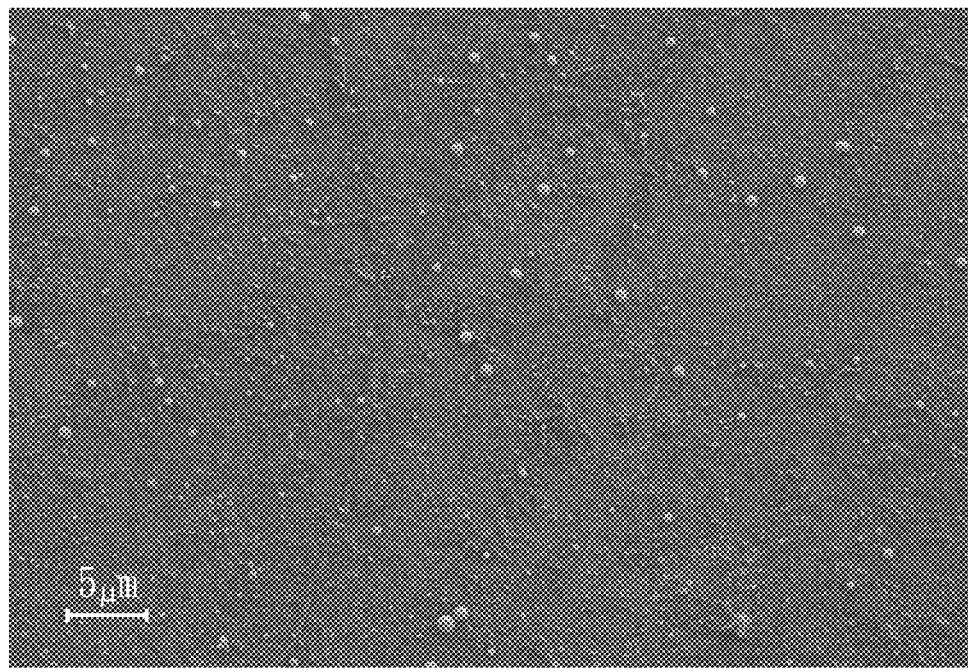
FIG. 5 is a SEM image of the experimental result of Group A3.
Figure 6:
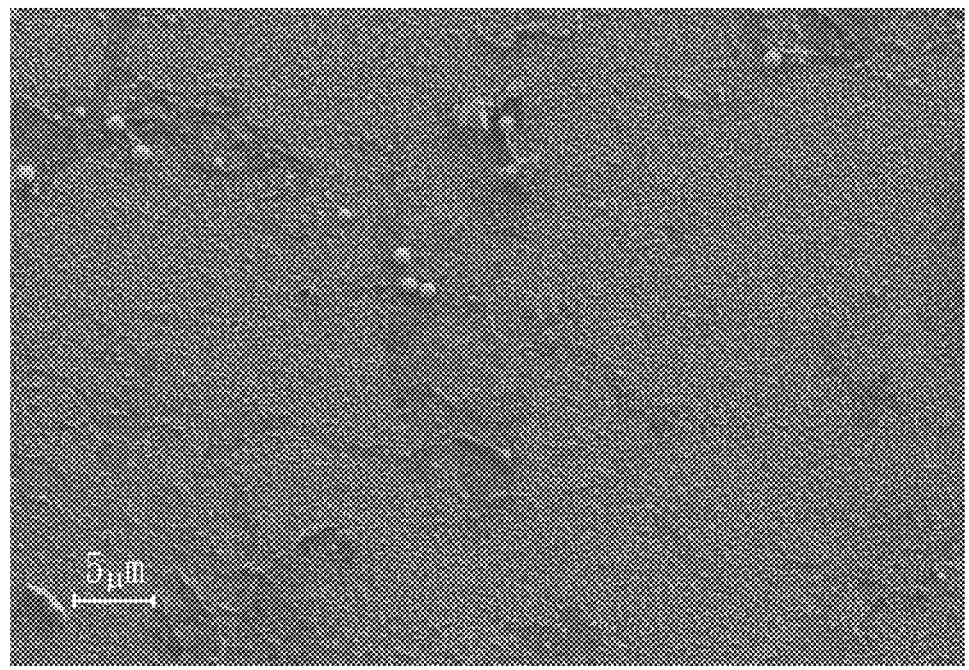
FIG. 6 is a SEM image of the experimental result of Group A4.

Please refer to FIGS. 3-6, which are the SEM images of the graphene-semiconductor hybrid panels of Group A1-A4. For Group A1-A3. As can be seen in the figures, the particles are deposited on the surface of the graphene sheet with uniform distribution. By using the graphene sheets with different numbers of graphene layers, the amount, sizes and distributing density of the particles may be regulated. It is noted that the graphene-semiconductor hybrid panel with 3 graphene layers (Group A2, as shown in FIG. 4) has the sizes and distribution of the gold particle being most uniform over Group A1-A3. Referring to the graphene-semiconductor hybrid panel of Group A4 as shown in FIG. 6, it is noted that the particle can also be deposited on the graphene sheet with its surface being modified by oxygen plasma. That is, the method for photodepositing the particle on the graphene-semiconductor hybrid panel in the present invention can be achieved with the graphene-semiconductor hybrid panel having pristine or modified graphene sheet.

In another experiment, the graphene-semiconductor hybrid panel with single graphene layer is prepared as the graphene-semiconductor hybrid panel of Group B and C. In Group B, the particle made of silver is deposited using an ethanol solution of 0.001 M silver nitrate and a UV light of 365 nm. In Group C, the particle made of manganese dioxide is deposited using an aqueous solution of 0.001 M potassium permanganate (VII) and a UV light of 365 nm.

Figure 7:
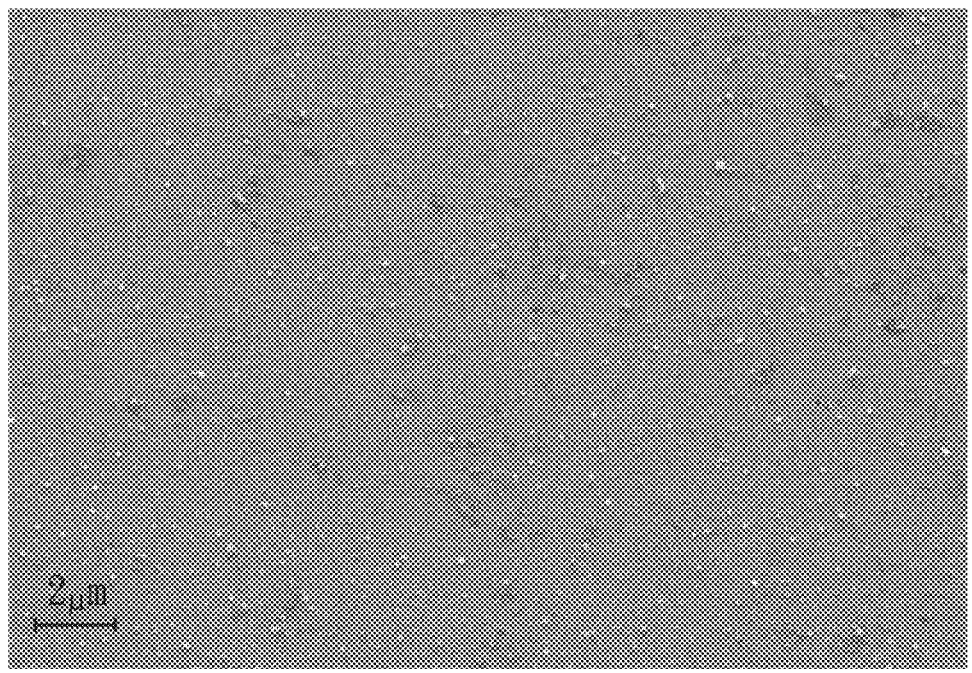
FIG. 7 is a SEM image of the experimental result of Group C.
Figure 8:
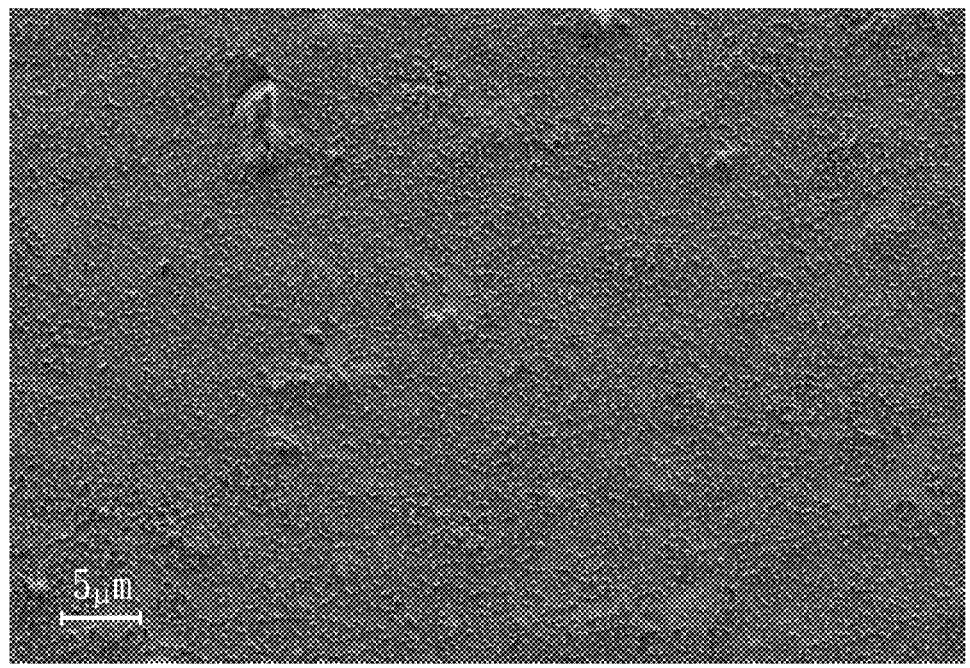
FIG. 8 is a SEM image of the experimental result of Group D.

The SEM images of the graphene-semiconductor hybrid panel of Group B and C are respectively shown as FIGS. 7 and 8. Accordingly, the method for photodepositing the particle on the graphene-semiconductor hybrid panel is capable of depositing the particle of silver or manganese dioxide. As a summary of the above, the method for photodepositing the particle on the graphene-semiconductor hybrid panel may actually deposit the particle made of various materials on the surface of both pristine and modified graphene sheets with uniform distribution of the particle.

Another set of experiments is carried out for validating the semiconductor structure in the present invention, where the particle is deposited on the charge transfer site, thus forming the semiconductor structure with excellent electrochemical activity.

In the Group D0, a gold-deposited semiconductor substrate is produced by photodepositing the gold particle on a surface of the semiconductor substrate without graphene sheet. The gold-deposited graphene-semiconductor hybrid panels of previous Group A1-A3 are taken as the semiconductor structures of Group D1-D3. Another semiconductor substrate without graphene sheet is taken as the control group (Group R). An ethanol solution of $10^{-5}$ M R6G (rhodamine 6G) is prepared as a sample solution, and another ethanol solution of $10^{-3}$ M R6G is prepared as a reference solution. A droplet of the sample solution is dropped on each of the gold-deposited semiconductor substrate and the semiconductor structures in Groups D0-D3, and a droplet of the reference solution is dropped on the semiconductor substrate of Group R. All of them are dried under ambient conditions. The Raman signal of R6G in Groups R and D0-D3 are acquired under a 633 nm He—Ne laser with a power of 2 mW.

Figure 9:
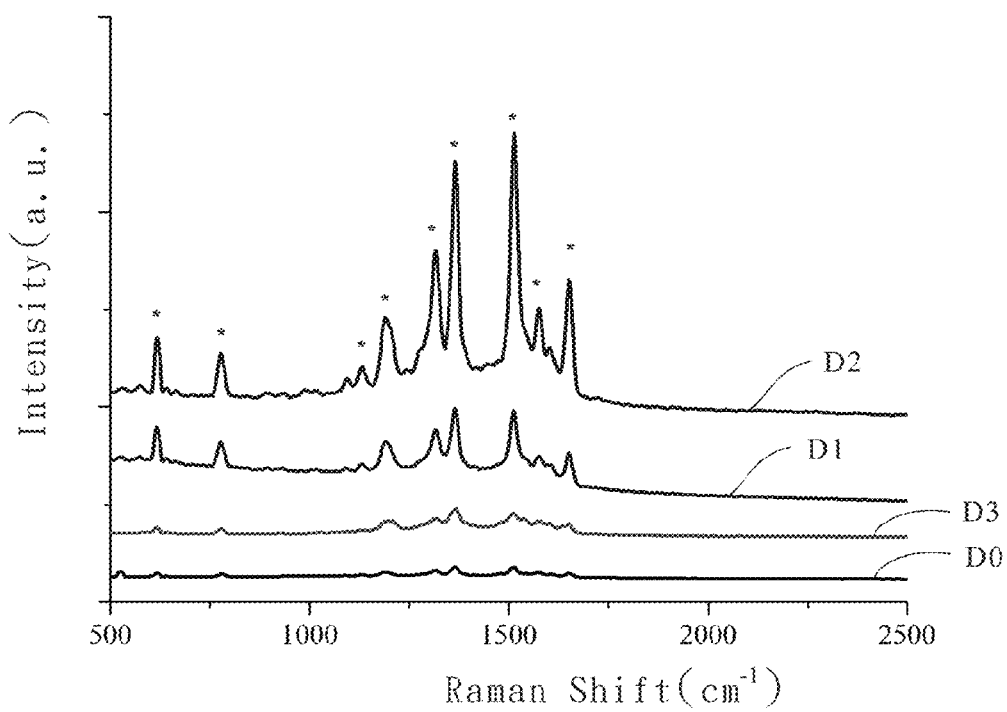
FIG. 9 shows the SERS results of Group D0-D3.

Please refer to FIG. 9, which shows the Raman signal results of Group D0-D3. The peaks labeled with the asterisk sign in the figure correspond to the vibration mode of R6G. Since the particle (which is made of gold in this experiment) is directly deposited on the surface of the graphene sheet, the charges may flow fluently through the semiconductor substrate, the graphene sheet and the particle. Thus, an excellent efficacy of surface plasmon resonance is provided by the graphene sheet and the particle.

Figure 10:
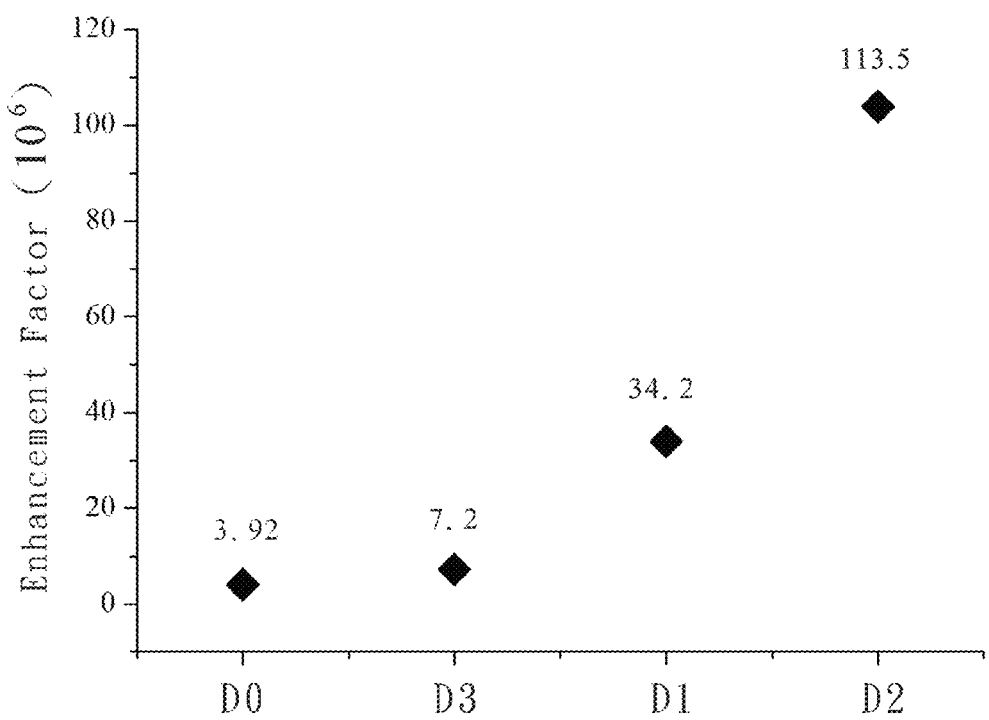
FIG. 10 shows the enhancement factors of Group D0-D3.

Please refer to FIG. 10, which shows the enhancement factor (EF) of Group D0-D3. The enhancement factor of SERS is defined as $EF=(I_{SERS}/I_R)/(N_R/N_{SERS})$, where $I_{SERS}$ and $I_R$ are the integrated intensity of the R6G peak at 1510 $cm^{-1}$ collected respectively of Group D0-D3 and Group R, and $N_{SERS}$ and $N_R$ are the numbers of molecules of Group D0-D3 and Group R respectively. According to this figure, the enhancements of Group D1-D3 are significantly higher than that of Group D0. The enhancement factor of Group D2 is about $10^8$, which is the largest one among all.

With reference to FIGS. 9 and 10, the function of the semiconductor structure of the present invention is confirmed. Since the particle is directly deposited on the graphene sheet, the charges are capable of flowing through the graphene sheet, the semiconductor substrate and the particle. Thus, the electrochemical activity of the particle is improved. The semiconductor structure may have an excellent SERS enhancement when the particle is made of gold, and may be used as the SERS substrate.

In conclusion, in the method for photodepositing the particle on the graphene-semiconductor hybrid panel, the semiconductor substrate is irradiated by the light source for generating the photoinduced electron and hole, and then the electron and hole are transferred to the graphene sheet. The precursor is reduced or oxidized by the electron or the hole to form the particle directly deposited on the surface of the graphene sheet. Thus, the function of directly depositing the particle on the surface of the graphene is achieved.

By using the method for photodepositing the particle on the graphene-semiconductor hybrid panel in the present invention, the particle is deposited on the surface of the graphene sheet by irradiation using the light source. Thus, the process of depositing the particle on the graphene sheet is simplified without the need of modifying the graphene.

Furthermore, according to the method for photodepositing the particle on the graphene-semiconductor hybrid panel in the present invention, the precursor is reduced or oxidized by the electron or hole generated in the semiconductor substrate and transferred by the graphene sheet. As such, the particle is deposited directly on the charge transfer site of the graphene sheet, thus providing an excellent charge transfer efficiency of the particle.

In addition, according to the method for photodepositing the particle on the graphene-semiconductor hybrid panel in the present invention, since the particle is deposited on the graphene-semiconductor hybrid panel by irradiation using the light source, the light source may be controlled to irradiate only a specific area to deposit the particle in the specific area. The method for photodepositing the particle on the graphene-semiconductor hybrid panel of the present invention is also capable of depositing the particle on a large-sized graphene sheet.

With accordance to the semiconductor structure in the present invention, since the particle is directly deposited on the surface of the graphene sheet, the charges may directly be transferred between the graphene sheet and the particle without flowing through the functional group, which is necessary in the conventional method. Thus, the electrochemical activity of the particle is improved.

Although the invention has been described in detail with reference to its presently preferable embodiments, it will be understood by one of ordinary skill in the art that various modifications can be made without departing from the spirit and the scope of the invention, as set forth in the appended claims.

What is claimed is:

1. A method for photodepositing a particle on a graphene-semiconductor hybrid panel, comprising:
   providing a graphene-semiconductor hybrid panel comprising a semiconductor substrate and a graphene sheet, wherein the graphene sheet is adhered to a surface of the semiconductor substrate;
   dipping the graphene-semiconductor hybrid panel in a fluid, wherein the fluid contains a precursor; and
   forming photoinduced electrons and holes in the semiconductor substrate by irradiating the semiconductor substrate using a light source, until the precursor has been reduced or oxidized to form a particle photodeposited on a surface of the graphene sheet by the photoinduced electrons or holes transferred to the graphene sheet, wherein the light source has an energy equal to or higher than a band gap of the semiconductor substrate.

2. The method for photodepositing the particle on the graphene-semiconductor hybrid panel as claimed in claim 1, wherein the graphene sheet is made by chemical vapor deposition and wet transfer.

3. The method for photodepositing the particle on the graphene-semiconductor hybrid panel as claimed in claim 1, wherein the semiconductor substrate is made of titanium dioxide or zinc oxide.

4. The method for photodepositing the particle on the graphene-semiconductor hybrid panel as claimed in claim 1, wherein the graphene sheet is formed of a graphene layer or a plurality of graphene layers.

5. The method for photodepositing the particle on the graphene-semiconductor hybrid panel as claimed in claim 4, wherein the graphene sheet is formed of three graphene layers.

6. The method for photodepositing the particle on the graphene-semiconductor hybrid panel as claimed in claim 1, wherein the particle is made of metal, alloy or metal oxide.

7. The method for photodepositing the particle on the graphene-semiconductor hybrid panel as claimed in claim 6, wherein the particle is made of gold, silver or manganese dioxide.

8. The method for photodepositing the particle on the graphene-semiconductor hybrid panel as claimed in claim 1, wherein the graphene sheet is made by chemical vapor deposition and wet transfer, wherein the semiconductor substrate is made of titanium dioxide, wherein the graphene sheet is formed of three graphene layers, and wherein the particle is made of gold.

\* \* \* \* \*